(12) United States Patent
Schwab et al.

(10) Patent No.: US 6,433,240 B1
(45) Date of Patent: *Aug. 13, 2002

(54) PREPARATION OF PROPENE AND, IF DESIRED, 1-BUTENE

(75) Inventors: Peter Schwab, Bad Dürkheim; Boris Breitscheidel, Limburgerhof; Carsten Oost, Bad Dürkheim; Ralf Schulz, Speyer; Michael Schulz, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/241,298

(22) Filed: Feb. 1, 1999

(30) Foreign Application Priority Data

Feb. 12, 1998 (DE) .......................... 198 05 716

(51) Int. Cl.$^7$ .............................. C07C 6/02; C07C 6/04

(52) U.S. Cl. .................... 585/646; 585/324; 585/313; 585/315; 585/316; 585/644; 585/647

(58) Field of Search ................... 585/324, 313, 585/315, 316, 644, 646, 647

(56) References Cited

U.S. PATENT DOCUMENTS

| | | | | |
|---|---|---|---|---|
| 3,531,545 A | * | 9/1970 | Garner et al. | 260/683.2 |
| 3,707,579 A | * | 12/1972 | Mongomery | 260/683 |
| 3,767,565 A | | 10/1973 | Banks | 208/93 |
| 3,776,974 A | * | 12/1973 | Gautier et al. | 260/683 D |
| 3,785,957 A | | 1/1974 | Banks | 208/49 |
| RE28,137 E | | 8/1974 | Turner et al. | 260/683 D |
| 4,709,115 A | * | 11/1987 | Jung et al. | 585/643 |
| 5,120,894 A | | 6/1992 | McCauley | 585/664 |
| 5,304,692 A | * | 4/1994 | Yamada et al. | 585/646 |

FOREIGN PATENT DOCUMENTS

| | | | |
|---|---|---|---|
| CA | 215426 | | 3/1998 |
| DE | 1940433 | | 2/1970 |
| EP | 304515 | | 3/1989 |
| EP | 691318 | * | 1/1996 |
| EP | 832867 | | 4/1998 |
| GB | 1216278 | * | 12/1970 |

OTHER PUBLICATIONS

Distillation Columns with Vertical Partitions, Kabel, Chem Eng. Technol. 10, pp. 92–98, 1987.*

*Hydrocarbon Processing*, vol. 26, No. 11, Nov. 1967, p. 232. Triolefin Process; Phillips Petrolelum Co.

*Hydrocarbon Processing*, vol. 55, No. 8, Aug. 1978, pp. 119–122. Olefin Disproportionation—New Routes to Petrochemicals.

* cited by examiner

*Primary Examiner*—Thuan D. Dang
(74) *Attorney, Agent, or Firm*—Keil & Weinkauf

(57) ABSTRACT

Propene and, if desired, 1-butene are prepared by first reacting 1-butene and 2-butene to give propene and 2-pentene in the presence of a metathesis catalyst containing at least one compound of a metal of transition group VIb, VIIb or VIII of the Periodic Table of the Elements. The propene and 2-pentene formed are subsequently separated, and the 2-pentene is then reacted to give propene and 1-butene in the presence of a metathesis catalyst containing at least one compound of a metal of transition group VIb, VIIb or VIII. The propene and 1-butene formed are subsequently separated, and at least some of the 1-butene is discharged or at least partly isomerized to give 2-butene in the presence of an isomerization catalyst. Undischarged 1-butene and the 2-butene formed are subsequently returned to the initial reaction step, together with that part of the $C_4$ fraction which was not reacted in the initial reaction step.

12 Claims, 2 Drawing Sheets

PREPARATION OF PROPENE AND, IF DESIRED, 1-BUTENE

CROSS-REFERENCES TO RELATED APPLICATIONS (Not applicable)

STATEMENT REGARDING FEDERALLY SPONSORED RESEARCH OR DEVELOPMENT (Not Applicable)

BACKGROUND OF THE INVENTION

1. Field of the Invention

The present invention relates to a process for preparing propene and, if desired, 1-butene by metathesis of olefins.

BRIEF SUMMARY OF THE INVENTION

Olefin metathesis (disproportionation) in its simplest form describes the reversible, metal-catalyzed rearrangement of olefins by cleavage and reformation of C=C double bonds. For example, olefins of the formulae $R^1$—CH=CH—$R^2$ and $R^3$—CH=CH—$R^4$ are reversibly reacted to form olefins of the formulae $R^1$—CH=CH—$R^3$ and $R^2$—CH=CH—$R^4$. In the metathesis of acyclic olefins, a distinction is made between self-metathesis in which an olefin is converted into a mixture of two olefins having different molar masses and cross0- or co-metathesis in which two different olefins react. An example of self-metathesis is the reaction of two molecules of propene to give ethene and 2-butene, as is performed, for. example, by the Phillips triolefin process, see Hydrocarbon Processing, Volume 46, November 1967, No. 11, p. 232. An example of cross-metathesis is the reaction of propene and 1-butene to give ethene and 2-pentene. If one of the reactants is ethene, the reaction is customarily referred to as an ethenolysis.

The metathesis reactions are carried out in the presence of catalysts. Suitable catalysts for this purpose are, in principle, homogeneous and heterogeneous transition metal compounds, in particular those of transition groups VI to VIII of the Periodic Table of the Elements, as well as homogeneous and heterogeneous catalyst systems in which these compounds are present.

DE-A-19 40 433 discloses the metathesis of 1-butene with 2-butene to form propene and 2-pentene, with $Re_2O_7/Al_2O_3$ being used as catalyst. The 2-pentene formed is reacted further with sodium hydride on potassium carbonate and ethene to give heptenes.

The metathesis of 1-butene and 2-butene to give propene and 2-pentene is mentioned in K. L. Anderson, T. D. Brown, Hydrocarbon Processing, Volume 55, August 1978, No. 8, pp. 119–122 as a secondary reaction in the synthesis of isoamylene.

EP-A-0 304 515 discloses a metathesis process for reacting 1-butene with 2-butene to give propene and pentenes, which is carried out in a reactive distillion apparatus using $Re_2O_7/Al_2O_3$ as catalyst.

U.S. Pat. No. 3,526,676 discloses the metathesis of 1-butene with 2-butene to give propene and pentene. It is carried out over $MoO_3$ and CoO on $Al_2O_3$.

U.S. Pat. No. 3,785,957 discloses a process for the production of fuel having a high octane number. In this process, an olefinic fuel is disproportionated together with ethylene, the product is fractionated into a propylene stream, a butene stream, a $C_5$- or $C_5$–$C_6$-olefin stream and a $C_{6+}$ or $C_{7+}$ fuel stream. The $C_5$- or $C_5$–$C_6$-olefin stream is disproportionated with ethene over a $WO_3/SiO_2$ fixed-bed catalyst to give propylene and butenes. The propylene obtained is disproportionated to form ethylene and butenes and the butenes are alkylated with isobutane.

U.S. Pat. No. 3,767,565 discloses a process for increasing the octane number of fuel in which a $C_5$ fraction of an olefinic fuel is reacted with ethylene in the presence of a catalyst comprising $WO_3/SiO_2$ and MgO to form ethylene, propylene, n-butenes and isobutenes. The propylene obtained is disproportionated and the resulting n-butenes are alkylated with isobutane.

EP-A-0 691 318 discloses an olefin metathesis process in which $C_5$-olefins and ethylene are reacted in the presence of a catalyst to give mixed $C_4$-olefins and propene. Thus, 2-methyl-2-butene is reacted with ethene to give isobutene and propene. A mixture of 2-pentenes and 2-methyl-2-butene is reacted to give a mixture of 1-butene, isobutene and propene.

2. Description of the Related Art

In the above processes, propene is prepared with addition of at least equimolar amounts of ethene. To achieve high propene selectivities, a large amount of ethene has to be circulated.

It is an object of the present invention to provide a process for preparing propene and, if desired, 1-butene as coupled product in variable amounts using $C_4$-olefins such as raffinate II.

We have found that this object is achieved by a process for preparing propene and, if desired, 1-butene by a) reacting 1-butene and 2-butene to give propene and 2-pentene in the presence of a metathesis catalyst comprising at least one compound of a metal of transition group VIb, VIIb or VIII of the Periodic Table of the Elements, b) subsequently separating the propene and 2-pentene formed, c) subsequently reacting the 2-pentene with ethene to give propene and 1-butene in the presence of a metathesis catalyst comprising at least one compound of a metal of transition group VIb, VIIb or VIII of the Periodic Table of the Elements, d) subsequently separating the propene and 1-butene formed, e) discharging at least some of the 1-butene formed and/or at least partly isomerizing the 1-butene formed to give 2-butene in the presence of an isomerization catalyst and subsequently returning the undischarged 1-butene and the 2-butene formed together with a part of the $C_4$ fraction not reacted in step a) to step a).

DETAILED DESCRIPTION OF THE INVENTION

Figure 1:
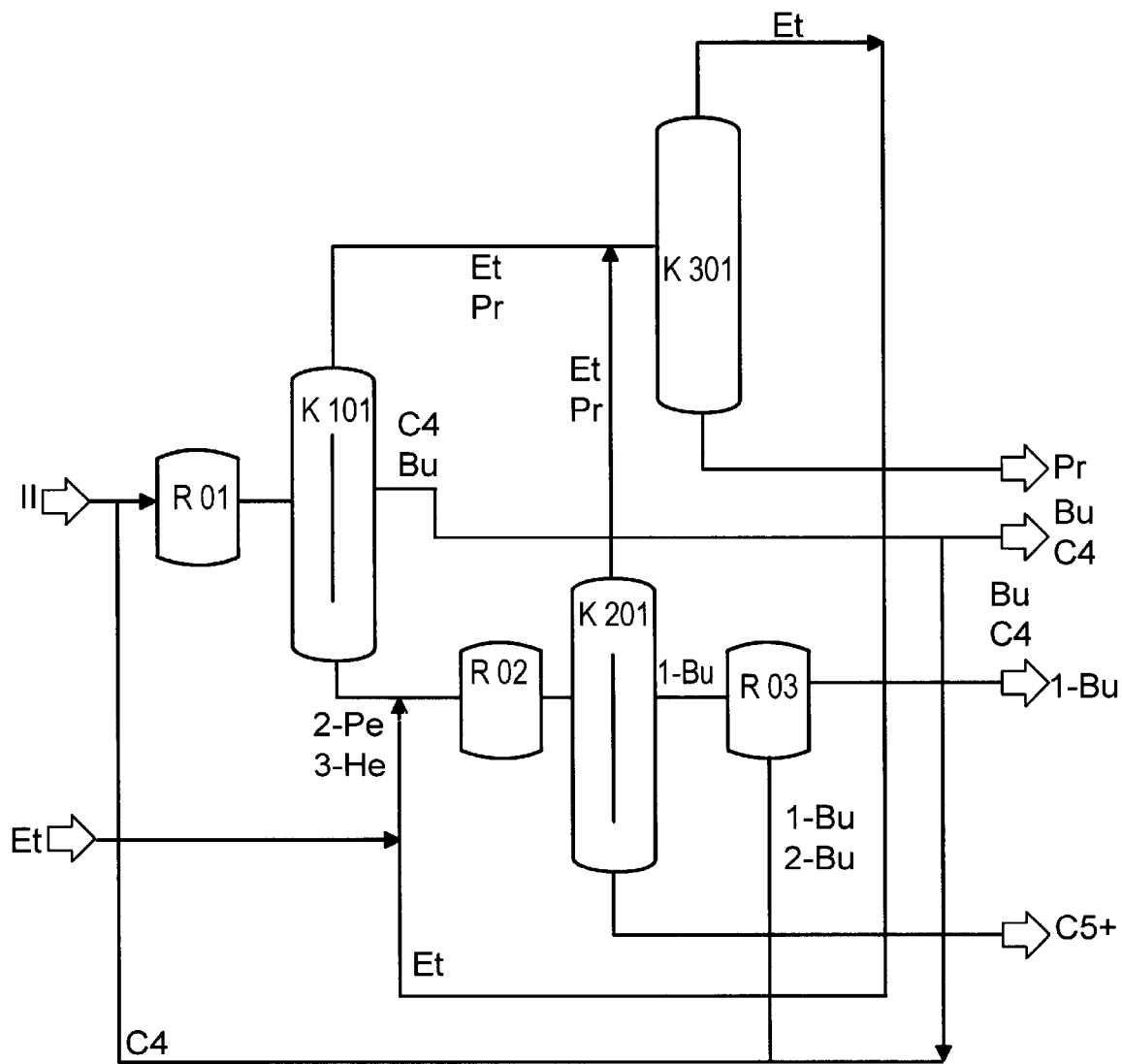
FIG. 1 of the drawings schematically illustrates one embodiment of the process of the present invention by means of a flow diagram.

The process of the present invention comprises 2 metathesis steps. In the first step, 1-butene and 2-butene are reacted to give propene and 2-pentene. In a second step, 2-pentene is then reacted with ethene to 1-butene and propene. According to one embodiment of the invention, the 1-butene is at least partially isomerized in the presence of an isomerization catalyst to give 2-butene and the resulting mixture of 1-butene and 2-butene is returned to the first reaction step. A part of the 1-butene can be discharged before the isomerization or can be conveyed past the isomerization reactor and combined with the output from the isomerization reactor. This, and also regulation of the conversion over the isomerization catalyst, can be used to set an optimum ratio of 1-butene to 2-butene at the inlet of the first metathesis reactor in order to achieve a maximum yield of propene. In this way, the raw material requirements in terms of ethene and $C_4$-olefins can be reduced by from about 5 to 15% compared to single-stage ethenolysis processes as are described, for example, in U.S. Pat. No. 3,660,506 and EP-A-0 273 817.

According to one embodiment, the 1-butene formed in step c) is at least partially isomerized in the presence of an isomerization catalyst to give 2-butene and the resulting mixture of 1-butene and 2-butene is returned to step a).

According to a further embodiment, at least some of the 1-butene formed in step c) is discharged and undischarged 1-butene is returned to step a).

The net reaction is thus the reaction of 2-butene with ethene to form 2 molecules of propene. According to one embodiment of the invention, the reaction of 2-pentene with ethene formally requires only equimolar amounts of starting materials in order to obtain the products in high yield. Thus, in contrast to the reverse triolefin process, the amount of ethene used can be kept small.

Both metathesis steps can be carried out as a reactive distillation, as is described below.

According to one embodiment of the invention, 1-butene and 2-butene can be used in the reaction as pure substances. According to another embodiment of the invention, the butenes are used in the form of a $C_4$ stream which originates, for example, from a cracker, in particular a stream cracker, or a refining process. This $C_4$ stream can comprise $C_4$-alkanes in addition to the butenes. According to an embodiment of the invention, use is made of a $C_4$ stream which consists of raffinate II. Raffinate II is here a fraction comprising 1-butene, cis/trans-2-butene, little or no isobutene and also n-butane and iso-butane. For example, raffinate II can comprise 80–85% by weight of olefins and 15–20% by weight of butanes, with, for example, 25–50% by weight of 1-butene, 30–55% by weight of 2-butene and at most 1–2% by weight of isobutene. According to an embodiment of the invention, the $C_4$ stream used has a butene content of from 20 to 100% by weight, preferably from 50 to 90% by weight, in particular from 70 to 90% by weight. The ratio of 1-butene to 2-butene is from 10:1 to 1:10, preferably from 3:1 to 1:3, in particular 1:1. According to one embodiment of the invention, the $C_4$ stream can contain small amounts of other hydrocarbons.

According to an embodiment of the invention, the starting material used can be any stream in which 1-butene and 2-butene are present. According to one embodiment of the invention, the 1-butene can originate from the synthesis of the present invention itself and be mixed with introduced 2-butene.

The $C_4$ feedstream used is preferably pre-purified before use in the process of the present invention in order to remove any traces of water, oxygenates, sulfur-containing compounds or chlorides which may be present. The removal is preferably carried out by passing the $C_4$ feedstream over absorber material such as aluminum oxide or molecular sieves, preferably NaX molecular sieve. The absorber materials are preferably present as a guard bed.

Apart from the reaction of 1-butene and 2-butene to form propene and 2-pentene, a small proportion of 3-hexene and ethene can be obtained as by-product. In addition, small amounts of higher-boiling compounds can also be present.

The small amounts of by-products, which according to an embodiment of the invention make up from 1 to 30% by weight, preferably from 5 to 20% by weight, of the amount of 2-pentene formed, do not interfere in the subsequent reaction so that, according to one embodiment of the invention, no purification of the 2-pentene to remove these by-products is necessary before the further reaction. According to one embodiment of the invention, the 2-pentene is used in pure form in the secondary reaction.

Thus, the expression "2-pentene" also includes those mixtures comprising not only 2-pentene but also small amounts of hexenes, in particular 3-hexene, and other higher-boiling compounds.

Correspondingly, the expression "butenes", "1-butene" and "2-butene" also includes a mixture which comprises not only the butene or butenes but also $C_4$-alkanes, in particular butanes.

A number of embodiments of the invention are illustrated below with the aid of the drawing, in which FIG. 1 schematically shows an embodiment of the process of the invention.

Figure 2:
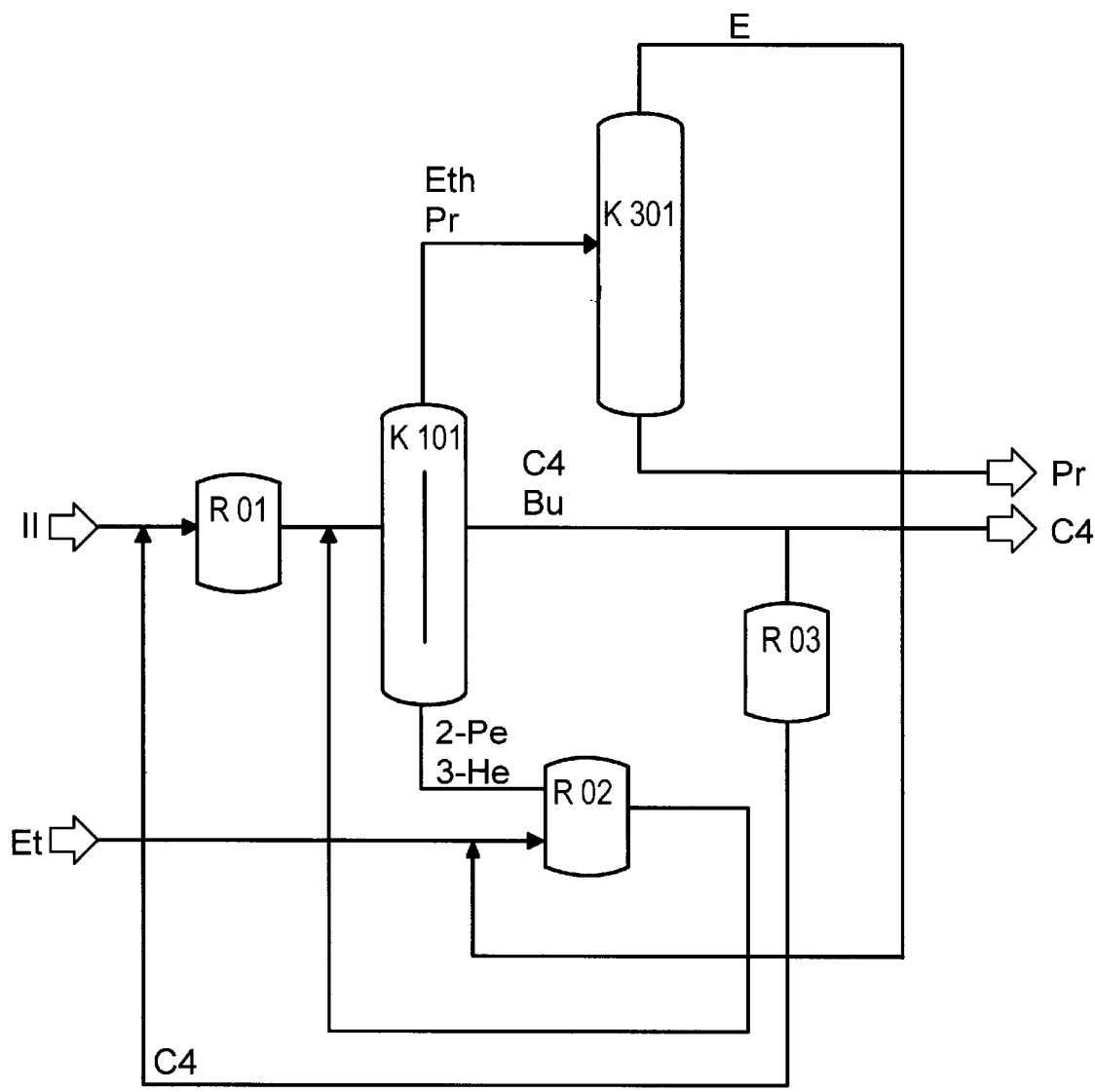
FIG. 2 of the drawings schematically illustrates an additional embodiment of the process of the present invention by means of a flow diagram.

FIG. 2 schematically shows a further embodiment of the process of the invention.

The abbreviations employed in the figures have the following meanings:

| | |
|---|---|
| 1-Bu: | 1-butene |
| 2-Bu: | 2-butene |
| Bu: | butanes |
| Et: | ethene |
| Pr: | propene |
| 2-Pe: | 2-pentene |
| 3-He: | 3-hexene |
| H: | high boilers |
| II: | raffinate II |
| C4: | C4 olefins |
| C5+: | olefins having 5 or more carbon atoms |
| R01: | reactor (metathesis) |
| R02: | reactor (metathesis) |
| R03: | reactor (isomerization) |
| K101: | distillation column (preferably a dividing wall column, side column or 2-column arrangement) |
| K201: | distillation column (preferably a dividing wall column, side column or 2-column arrangement) |
| K301: | distillation column |

Described below is a preferred embodiment of the process of the invention, comprising a) reaction of 1-butene and 2-butene to give propene and 2-pentene in the presence of a metathesis catalyst comprising at least one compound of a metal of transition group VIb, VIIb or VIII of the Periodic Table of the Elements, b) subsequent separation of the propene and 2-pentene formed, c) subsequent reaction of the 2-pentene with ethene to give propene and 1-butene in the presence of a metathesis catalyst comprising at least one compound of a metal of transition group VIb, VIIb or VIII of the Periodic Table of the Elements, d) subsequent separation of the propene and 1-butene formed, e) at least partial isomerization of the 1-butene formed to give 2-butene in the presence of an isomerization catalyst and subsequent return of the 1-butene and the 2-butene formed together with a part of the $C_4$ fraction not reacted in step a) to step a).

This embodiment is shown in FIG. 1.

In a first reactor R01, 1-butene and 2-butene are reacted in the presence of the metathesis catalyst of the present invention to give propene and 2-pentene. For this purpose, a raffinate II stream is fed to the reactor. The reactor is followed by a distillation column K101, configured as a dividing wall column, side column or 2-column arrangement, at the top of which propene and ethene formed as by-product are removed. Unreacted raffinate II is taken off at the middle offtake and some of it is returned to the feed stream of raffinate II. Some of it may also be discharged. 2-Pentene formed as by-product as well as high boilers are taken off at the bottom of K101. The bottoms are then fed together with added ethene to a reactor R02 which again contains a metathesis catalyst of the present invention. In this reactor R02, the reaction of 2-pentene with ethene to give 1-butene and propene takes place. The reaction product from reactor R02 is fed to a distillation column K201, configured as a dividing wall column, side column or 2-column arrangement, at the top of which propene and unreacted ethene are taken off. Some of the 1-butene formed may be taken off at the middle offtake and at least some of it is preferably fed to the isomerization reactor R03. Unreacted 2-pentene and also, as by-products, 3-hexene and high boilers are obtained at the bottom of K201. These are discharged or preferably returned to R02. The mixtures of propene and by-product ethene taken off at the top of K101 and K201 are fractionated in a further distillation column K301. Ethene is obtained at the top of K301 and this is preferably returned to the reactor R02. In the isomerization reactor R03, the 1-butene is at least partially isomerized to give 2-butene over an isomerization catalyst, and the isomerization mixture is returned to the reactor R01. The broken line in R03 indicates the possible discharge of the 1-butene. The propene obtained at the bottom of K301 is, in addition to any 1-butene discharged from K201, the desired reaction product of the process of the present invention. K101 and K201 are designed such that a low-boiling phase, in particular a $C_{2/3}$ phase comprising ethene and propene, is taken off at the top of the column. $C_4$ streams, in particular butenes and butanes, are taken off as intermediate-boiling phase. As bottoms, $C_{5}$-hydrocarbons are discharged.

Between the steps b) and c), the high-boiling product comprising 2-pentene and 3-hexene which has been separated off can be subjected to a distillation to separate 2-pentene and 3-hexene. The distillation can be carried out in any suitable apparatus. The 2-pentene-containing fraction is then fed to the reactor R02. The 3-hexene can be discharged and, for example, fed to a dimerization to give a $C_{12}$-olefin mixture.

The reactors R01, R02 and R03 can be any suitable reactors. They can serve for continuous or batchwise operation. Thus, according to one embodiment, they can be pressure vessels such as glass pressure vessels, while according to a further embodiment they can be tube reactors or reaction columns. Tube reactors are preferred.

According to an embodiment of the invention, the total conversion in R01 is from 20 to 90%, preferably from 50 to 80%.

According to an embodiment of the invention, the total conversion in R02 is from 20 to 100%, preferably from 60 to 90%.

The reaction in R01 preferably takes place in the liquid phase. Here, pressure and temperature are selected such that the reactants remain in the liquid phase.

According to an embodiment of the invention, the temperature in R01 is from 0 to 150□° C., preferably from 20 to 80□° C. According to an embodiment of the invention, the pressure is from 1 to 200 bar, preferably from 5 to 30 bar. The reaction in R02 (ethenolysis) is, according to an embodiment of the invention, carried out at from 0 to 150□° C., preferably from 20 to 80□° C., under an ethene pressure of from 1 to 200 bar, preferably from 20 to 80 bar. Further ethene can be injected continuously so that a constant pressure is maintained.

The reactions in R01 and R02 can be carried out for a time of from one second to ten hours, preferably from 1 to 60 minutes.

The distillation columns K101 and K201 are, according to an embodiment of the invention, columns which allow separation of a hydrocarbon stream into $C_{2/3}$ streams, $C_4$ streams and $C_{5+}$ streams. The columns can be designed as dividing wall columns, side columns or as 2-column arrangements. According to an embodiment of the invention, K301 is a column which allows the separation of ethene and propene. According to one embodiment of the invention, the reactor R01 is combined with the distillation column K101 to form a reactive distillation apparatus. Here, the reaction is carried out directly in the distillation column. The catalyst is present in the reaction column so that the distillation is carried out simultaneously with the reaction or immediately thereafter. A corresponding process is known under the name "reactive distillation".

According to one embodiment, reactor R02 and distillation column K201 are combined to form a reactive distillation apparatus in which the reaction and distillation are combined as in the above-described reactive distillation.

According to one embodiment of the invention, both reactions take place in reactive distillation apparatuses. Both reactions are equilibrium reactions so that, according to one embodiment of the invention, the process products are removed as quickly as possible from the equilibrium to achieve as high as possible a conversion. This is possible, in particular, when using reactive distillation apparatuses.

A further embodiment of the process of the present invention is shown in FIG. 2. FIG. 2 shows a process for preparing propene by a) reacting 1-butene and 2-butene to give propene and 2-pentene in the presence of a metathesis catalyst comprising at least one compound of a metal of transition group VIb, VIIb or VIII of the Periodic Table of the Elements, b) subsequently separating the propene and 2-pentene formed and the unreacted butenes, c) subsequently reacting the 2-pentene with ethene to give propene and 1-butene in the presence of a metathesis catalyst comprising at least one compound of a metal of transition group VIb, VIIb or VIII of the Periodic Table of the Elements, d) subsequently transferring the unreacted mixture to step b) to separate the propene and 1-butene formed, e) discharging at least some of the unreacted $C_4$ fraction separated off in step b) and/or at least partly isomerizing the 1-butene present in this $C_4$ fraction to give 2-butene in the presence of an isomerization catalyst and subsequently returning the mixture obtained to step a).

As regards the reaction conditions, what has been said above in relation to the process as shown in FIG. 1 applies analogously. The mixture obtained from the second metathesis reactor R02 is returned directly to the distillation column K101. At least some of the intermediate-boiling product comprising $C_4$-olefins and butanes obtained from column K101 is discharged and/or at least partly converted in the isomerization reactor R03 in which 1-butene is isomerized to 2-butene. The output from the isomerization reactor R03 is returned to step a), i.e. the metathesis reactor R01. In this process variant, the distillation column K201 can be dispensed with.

Metathesis Catalyst

All suitable metathesis catalysts can be used in R01 and R02 in the process of the present invention.

According to an embodiment of the invention, the catalyst is a heterogeneous catalyst, in particular a supported catalyst. According to an embodiment of the invention, the catalyst comprises at least one compound of a metal of transition group VIb, VIIb or VIII of the Periodic Table of the Elements. The catalyst preferably comprises a ruthenium compound and/or rhenium compound. Such catalysts are described, for example, in K. J. Ivin, I. C. Mol, Olefin Metathesis and Metathesis Polymerization, 2nd Edition, Academic Press, New York, 1996; G. W. Parshall, S. D. Ittel, Homogeneous Catalysis, 2nd Edition, 1992, John Wiley & Sons, New York, Chichester, Brisbane, Toronto, Singapore, p. 217ff, R. H. Grubbs in Progr. Inorg. Chem., S. Lippard (ed.), John Wiley & Sons, New York, 1978, Vol. 24, 1–50; R. H. Grubbs in Comprehensive Organomet. Chem., G. Wilkinson (ed.), Pergamon Press Ltd., New York, 1982, Vol. 8, 499–551; D. S. Breslow, Prog. Polym. Sci. 1993, Vol. 18, 1141–1195.

According to an embodiment of the invention, the metal compound is a metal oxide, partial oxide with additional organic radicals or a carbonyl compound.

According to one embodiment of the invention, a homogeneous catalyst is used. The catalyst is here at least one compound of a metal of transition group VIb, VIIb or VIII of the Periodic Table of the Elements. Preference is given to using rhenium or ruthenium in the metal compounds.

The metal compound is preferably an oxide of rhenium, in particular $Re_2O_7$.

Support

According to an embodiment of the invention, the catalysts of the present invention comprise a support. Supports employed here are, in particular, inorganic supports such as $Al_2O_3$, in particular $\square$-$Al_2O_3$, $SiO_2$, $Fe_2O_3$, or mixtures thereof such as $SiO_2/Al_2O_3$, $B_2O_3/SiO_2/Al_2O_3$ or $Fe_2O_3/Al_2O_3$.

The metal oxide content on the support is, according to one embodiment of the invention, from 1 to 20% by weight, preferably from 3 to 15% by weight, in particular from 8 to 12% by weight, based on the total weight of the supported catalyst.

The catalyst used is preferably $Re_2O_7$ on $Al_2O_3$, $SiO_2/Al_2O_3$, $SiO_2/Al_2O_3/Fe_2O_3$ or $B_2O_3/Al_2O_3$. The proportion of metal oxide here is preferably from 1 to 20% by weight, particularly preferably from 3 to 10% by weight. According to one embodiment of the invention, $MeReO_3$ is used in place of $Re_2O_7$ or in admixture therewith.

According to the present invention, particular preference is given to using $Re_2O_7$ on $Al_2O_3$.

According to one embodiment of the invention, the catalysts are used in freshly calcined form and then require no further activation, for example by means of alkylating agents. Deactivated catalysts can, according to the present invention, be regenerated by burning off carbon residues, for example at 550$\square$° C. in a stream of air and cooling under argon.

The reactions of the present invention can be carried out in the presence of a solvent, for example a hydrocarbon solvent. According to a preferred embodiment of the invention, the reactions are carried out without further added solvent.

Isomerization Catalyst

As isomerization catalyst, it is possible to use all catalysts which catalyze the isomerization of 1-butene to 2-butene. Suitable isomerization catalysts are, in principle, any homogeneous or heterogeneous noble metal compounds, in the presence or absence of hydrogen, as described, for example, in A. J. Hubert, H. Reimbinger, Synthesis 1970,1,405.

For example, the isomerization can be carried out as described in U.S. Pat. No. 3,592,868 over $RuO_3$ on an inorganic support such as $SiO_2$, $Al_2O_3$ or $TiO_2$ or mixed supports. U.S. Pat. Nos. 4,684,760 and 4,889,840 describe mixed catalysts comprising magnesium oxide, zirconium oxide and an alkali metal oxide on an inorganic support. EP-A-0 129 899 and DE-A-34 27 979 describe suitable phosphoric acids and phosphate-containing compounds and also zeolites of the pentasil type or zeolites doped with transition metals. The zeolites of the ZSM type, e.g. ZSM-22, ZSM-23 or ZSM-35, described in U.S. Pat. No. 5,177,281 are advantageous in terms of operating life of the catalyst and reaction conditions. Particularly active palladium catalysts, for example on $Al_2O_3$ as support, are described in U.S. Pat. No. 3,531,545.

The isomerization catalyst is preferably a heterogeneous catalyst comprising one compound of a noble metal of the transition series of the Periodic Table of the Elements which can be present in the form of the metal or an oxide or mixed oxide. Furthermore, compounds of a metal of main group I or II of the Periodic Table of the Elements are also suitable, and can be present as oxide or mixed oxide.

Preference is given to using a metal or metal oxide of transition group VII or VIII of the Periodic Table of the Elements, which can be present on a support, as isomerization catalyst in an inert gas atmosphere or in the presence of hydrogen.

The alkali metal oxide and/or alkaline earth metal oxide catalysts which are preferred according to the present invention are preferably prepared by impregnation of inorganic supports such as $SiO_2$, $Al_2O_3$, $ZrO_2$, $TiO_2$ or mixtures thereof with alkali metal and/or alkaline earth metal compounds, subsequent drying and calcination to give the corresponding oxides. Deactivated catalyst can be regenerated in a simple way by burning-off coke residues at temperatures above 350° C. in a stream of air and cooling in an inert gas atmosphere.

The isomerization catalyst which is particularly preferably used is PdO on an $Al_2O_3$ or $SiO_2$ support in the presence of hydrogen, where the Pd content is from 0.1 to 5% by weight, based on the total weight of the catalyst.

When using the abovementioned catalysts, the $C_4$ intermediate-boiling fraction from the column K201 is converted by partial isomerization into a mixture of 1-butene and 2-butenes and returned to the cross-metathesis in R01 to increase the propene yield. Alternatively, if the raffinate II feed stream has an appropriate purity, 1-butene can be obtained without further work-up. It can then be used, for example, for preparing polymers such as LLDPE copolymers, HDPE copolymers, poly-1-butene or for preparing butylene oxide.

In the isomerization, just as in the metathesis reactions in R01 and R02, the conditions are selected such that the reactants are present in the liquid phase. The temperature is thus preferably from 0 to 200° C., particularly preferably from 50 to 150° C. The pressure is preferably from 2 to 200 bar. The isomerization is preferably complete after from 1 second to 1 hour, preferably from 5 to 30 minutes. It can be carried out continuously or batchwise, and the reactors can, like the metathesis reactors, be glass pressure vessels, tube reactors or distillation columns. Here too, preference is given to using tube reactors.

The invention also provides an apparatus for carrying out the process described. One apparatus for carrying out the process as shown in FIG. 1 comprises a metathesis reactor (R01) for reacting 1-butene with 2-butene whose outlet leads to a distillation column (K101), which can be configured as a dividing wall column, for separating $C_{2/3}$ low-boiling, $C_4$ intermediate-boiling and $C_5^+$ high-boiling phases, where the low boiler outlet leads to a column (K301) for separating ethene and propene, the intermediate boiler outlet leads to the reactor (R01) or to discharge and the high boiler outlet leads to a reactor (R02) for reacting 2-pentene with ethene whose outlet leads to the column (K101) or to discharge, where the ethene outlet from the column (D3) and an ethene feed line lead to the reactor (R2).

An apparatus for carrying out the process as shown in FIG. 1 comprises a metathesis reactor (R01) for reacting 1-butene with 2-butene whose outlet leads to a distillation column (K101), which can be configured as a dividing wall column, a side column or as a 2-column arrangement, for separating $C_{2/3}$ low-boiling, $C_4$ intermediate-boiling and $C_5^+$ high-boiling phases, where the low boiler outlet leads to a column (K301) for separating ethene and propene, the intermediate boiler outlet leads to the reactor (R01) or to discharge and the high boiler outlet leads to a reactor (R02) for reacting 2-pentene with ethene whose outlet leads to a distillation column (K201), which can be configured as a dividing wall column, a side column or as a 2-column arrangement, for separating $C_{2/3}$ low-boiling, $C_4$ intermediate-boiling and $C_5^+$ high-boiling phases, where the low boiler outlet leads to the column (K301), the intermediate boiler outlet leads to an isomerization reactor (R03) for the partial isomerization of 1-butene to 2-butene and, if desired, additionally to discharge, where the outlet of the isomerization reactor (R03) together with the intermediate boiler outlet from (K101) leads to the reactor (R01) and the high boiler outlet leads to discharge, where the ethene outlet from the column (K301) and an ethene feed line lead to the reactor (R02).

EXAMPLES

Continuous Experiments on the Synthesis of Propene from Raffinate II

Example 1

Continuous Experiment on the Cross-metathesis of 1-butene with 2-butene in Raffinate II Raffinate II (40% of 1-butene, 45% of cis/trans-2-butene) is passed continuously through a tube reactor R01 charged with $Re_2O_7/Al_2O_3$ heterogeneous catalyst at 60° C., 25 bar and a space velocity over the catalyst of 4500 kg/m² h. The reaction product is separated by means of pressure distillation K101 (20 bar) into a C⅔ low-boiling phase, an intermediate-boiling fraction comprising C4-olefins and butanes and a high-boiling fraction comprising 2-pentene and 3-hexene. The percentages reported are by mass:

| | C2/3 | C4 | C5/6 |
|---|---|---|---|
| % m/m | 21 | 56 | 23 |

Example 2

Continuous Experiments on the Ethenolysis of the C5/C6 High-boiling Product

The high-boiling product comprising 2-pentene and 3-hexene from K101 is passed continuously through a tube reactor R02 charged with $Re_2O_7/Al_2O_3$ heterogeneous catalyst at 60° C. and 60 bar of ethene (starting material ratio C2:C5,C6=1.1:1) at a mean residence time of 5 minutes. The reaction product is separated by means of pressure distillation K201 (20 bar) into a C⅔ low-boiling phase, an intermediate-boiling fraction comprising 1-butene and a high-boiling fraction comprising unreacted 2-pentene and 3-hexene. The percentages reported are by mass:

| | C2/3 | 1-butene | C5/6 |
|---|---|---|---|
| % m/m | 41 | 52 | 7 |

Example 3

Continuous Partial Isomerization of 1-butene

The intermediate-boiling product comprising 1-butene from column K201 is passed continuously in the presence of 0.1 mol % of hydrogen through a flow tube charged with $PdO/Al_2O_3$ heterogeneous catalyst at 100° C. and 15 bar at a mean residence time of 30 minutes. The reaction product is analyzed by gas chromatography and consists of 60% of 1-butene and 40% of 2-butenes.

We claim:
1. A process for preparing propene and optionally 1-butene by
   a) reacting a $C_4$ fraction of 1-butene and 2-butene to give propene and 2-pentene in the presence of a metathesis catalyst comprising at least one compound of a metal of transition group VIb, VIIb or VIII of the Periodic Table of the Elements;
   b) subsequently separating the propene and 2-pentene formed from the $C_4$ fraction in step a);
   c) subsequently reacting the 2-pentene from step b) with ethene to give propane and 1-butene in the presence of a metathesis catalyst comprising at least one compound of a metal of transition group VIb, VIIb or VIII of the Periodic Table of the Elements;
   d) subsequently separating the propene and 1-butene formed in step c);
   e) partially isomerizing at least some of the 1-butene from step d) in the presence of an isomerization catalyst to give 2-butene and returning the resulting mixture of 1-butene and 2-butene to step a); and
   f) discharging the propane from steps b) and d).
2. A process as claimed in claim 1, wherein at least some of the 1-butene formed in step c) is discharged and undischarged 1-butene is returned to step a).
3. A process as claimed in claim 1, wherein step b) is a distillation which is carried out in a dividing wall column, a side column, or a 2-column arrangement in which a propene-containing low-boiling phase is obtained, and/or wherein step d) is a distillation which is carried out in a dividing wall column in which a propene-containing low-boiling phase, a 1-butene-containing intermediate boiling phase and a 2-pentene-containing bottom phase are obtained.

4. A process as claimed in claim 1, wherein the reaction in steps a) and/or c) is not carried to completion so that in step b) and/or d) a $C_{2/3}$-containing low-boiling phase, a $C_4$ intermediate-boiling phase and a $C+_5$-containing bottom phase are obtained, wherein the low-boiling phases, which are combined, are separated by distillation into $C_2$ and $C_3$ phases and the $C_2$ phase is returned to step c), at least some of the intermediate-boiling phases, which are combined, are returned to step a) and at least some of the bottom phases, which are combined, are returned to step c).

5. A process as claimed in claim 1, wherein 1-butene and 2-butene are used as a mixture in a $C_4$ stream, from a cracker or a refinery, as raffinate II, and wherein the $C_4$ stream is passed over absorber materials before the reaction to purify it.

6. A process as claimed in claim 5, wherein the molar ratio of 1-butene to 2-butene is from 10:1 to 1:10.

7. A process as claimed in claim 1, wherein the metathesis catalyst is a heterogeneous metathesis catalyst comprising a rhenium or ruthenium compound on an inorganic support.

8. A process as claimed in claim 7, wherein the metathesis catalyst comprises $Re_2O_7$ on an $Al_2O_3$ support, with the rhenium oxide content being from 1 to 20% by weight, based on the total weight of the catalyst.

9. A process as claimed in claim 1, wherein the reaction of 1-butene and 2-butene and/or the reaction of 2-pentene with ethene are carried out as a reactive distillation.

10. A process as claimed in claim 1, wherein the isomerization catalyst used is a noble metal compound or its oxide, which is present on a support, in the presence of an inert gas or hydrogen atmosphere.

11. A process as claimed in claim 1, wherein, between steps b) and c), a high-boiling product comprising 2-pentene and 3-hexene, which has been separated off, is subjected to a distillation to separate the 2-pentene and 3-hexene.

12. A process for preparing propene, which process comprises a) reacting 1-butene and 2-butene to give propene and 2pentene in the presence of a metathesis catalyst comprising at least one compound of a metal of transition group VIb, VIIb or VIII of the Periodic Table of the Elements, b) subsequently separating the propene and 2-pentene formed and the unreacted butenes, c) subsequently reacting the 2-pentene with ethene to form propene and 1-butene in the presence of a metathesis catalyst comprising at least one compound of a metal of transition group VIb, VIIb or VIII of the Periodic Table of the Elements, d) subsequently transferring unreacted mixture from step c) to step b) to separate the propene and 1-butene formed, e) discharging at least some of the unreacted butenes separated off in step b) and/or at least partly isomerizing the 1-butene present in this butene fraction to give 2-butene in the presence of an isomerization catalyst and subsequently returning the mixture obtained to step a), and f) discharging the propene from steps b) and d).

* * * * *